US008646910B1

(12) United States Patent
Schenkein

(10) Patent No.: US 8,646,910 B1
(45) Date of Patent: Feb. 11, 2014

(54) VISION TRAINING METHOD AND APPARATUS

(76) Inventor: Joyce Schenkein, New York, NY (US)

( * ) Notice: Subject to any disclaimer, the term of this patent is extended or adjusted under 35 U.S.C. 154(b) by 281 days.

(21) Appl. No.: 13/024,138

(22) Filed: Feb. 9, 2011

Related U.S. Application Data

(63) Continuation of application No. 12/955,573, filed on Nov. 29, 2010, now abandoned.

(60) Provisional application No. 61/264,781, filed on Nov. 27, 2009.

(51) Int. Cl.
*A61B 3/00* (2006.01)

(52) U.S. Cl.
USPC .......... 351/203; 351/246

(58) Field of Classification Search
USPC .......... 351/200, 203, 246
See application file for complete search history.

(56) References Cited

U.S. PATENT DOCUMENTS

| | | | | |
|---|---|---|---|---|
| 4,971,434 | A | 11/1990 | Ball | |
| 5,035,500 | A | 7/1991 | Rorabaugh et al. | |
| 5,363,154 | A | 11/1994 | Galanter et al. | |
| 5,534,953 | A | 7/1996 | Schmielau | |
| 5,589,897 | A | 12/1996 | Sinclair | |
| 6,364,486 | B1 | 4/2002 | Ball et al. | |
| 6,379,370 | B1 | 4/2002 | Feinsod | |
| 6,464,356 | B1 | 10/2002 | Sabel et al. | |
| 7,004,912 | B2 | 2/2006 | Polat | |
| 7,321,796 | B2 | 1/2008 | Fink et al. | |
| 7,367,671 | B2 | 5/2008 | Sabel | |
| 7,549,743 | B2 | 6/2009 | Huxlin et al. | |
| 7,753,524 | B2 | 7/2010 | Sabel | |
| 2008/0013047 | A1* | 1/2008 | Todd et al. | 351/203 |
| 2008/0278682 | A1* | 11/2008 | Huxlin et al. | 351/203 |

FOREIGN PATENT DOCUMENTS

DE 9305147 U1 9/1994

OTHER PUBLICATIONS

Beatty, J., The Human Brain : Essentials of Behavioral Neuroscience, Sage Publications, p. 170-173 (2001).
Bodis-Wollner, I, Atlin, A., Wolkstein, M & Raab, E, Visual association cortex in man; pattern evoked occipital potentials in a blind boy,Science vol. 198 pp. 629-631 (1977).
Harrington, D.O.,The visual fields, Second Ed., Mosby, St. Louis, pp. 61-63, (1964).
Hein, A. et al., Development and Segmentation of Visually Controlled Movement by Selective Exposure During Rearing, J.Comparative Physiological Psychology,73(2),pp. 181-187(1970).
Held R., Plasticity in Sensory-Motor Systems, Sceintific American, vol. 213, No. 5, pp. 84-94 (1965).
Horton, J.C., Dissapointing results from Nova Vision's Visual restoration therapy, Br. J. Ophthalmology vol. 89, No. 1, pp. 1-2, (2005).
Humphrey, N.K. & Weiskrantz, L., Vision in monkeys after removal of striate cortex, Nature, vol. 215, pp. 595-597, (1967).
Humphrey. N.K., Vision in a monkey without striate cortex: a case study, Perception, vol. 3 241-255. (1974).
Miller, M., Pasik, P. & Pasik, T. Extrageniculostriate vision in the monkey VII: Contrast Sensitivity Functions. J. Neurophysiol vol. 43 1510-1526 (1980).
Perenin, M.T. et al.,Visual function in the hemianopic field following early cerebral hemidecortication in man I. Spatial localization, Neuropsychologia,vol. 16,pp. 2-12 (1978).
Richards W., Visual processing in Scotomata, Exp Brain Res., vol. 17 No. 4, pp. 333-347 (1973).

* cited by examiner

*Primary Examiner* — James Greece
(74) *Attorney, Agent, or Firm* — Ohlandt, Greeley, Ruggiero & Perle, L.L.P.

(57) ABSTRACT

The present invention concerns a method and device for the training of human vision. In particular, the invention involves the use of multimodal stimulation and principles of biofeedback to aid in the detection of visual targets. The intended population to benefit from this device are those who have experienced stroke or compromise to areas of the visual system responsible for conscious sight. Such patients may show either visual inattention or partial to complete blindness in both eyes. Biofeedback is also used to assist in training of sight.

32 Claims, 8 Drawing Sheets

MENU OPTIONS

Fig 3A . TARGET PARAMETERS:

A. SHAPE : CIRCLE , CUSTOM,
CHECKERBOARD : (2x2 , 3x3)

B. COLOR :
BLACK or WHITE
BLACK/WHITE DARK GREY/LIGHT GREY
(RESEARCH OPTIONS : RED/GREEN , BLUE/YELLOW)

C. SIZE :
- LARGE, MEDIUM, SMALL,
- CUSTOM SIZE (RESEARCH)

D .TEMPORAL RATE :
- DEFAULT (.5 HZ)
- CUSTOM VARIABLE (RESEARCH)

Fig 3B. BACKGROUND SCREEN COLOR

- BLACK
- WHITE
- RESEARCH : (RED,GREEN, BLUE/YELLOW)
- LIGHT GREY
- DARK GREY

Fig 3C . SAMPLE BEGINNER DEFAULT TARGET

- LARGE , WHITE TARGET/BLACK BACKGROUND
- LARGE , BLACK TARGET/WHITE BACKGROUND

Fig. 3

TRIAL FORMAT

Search Paths
Baseline
After 1 month

S1
S2
S1
S2

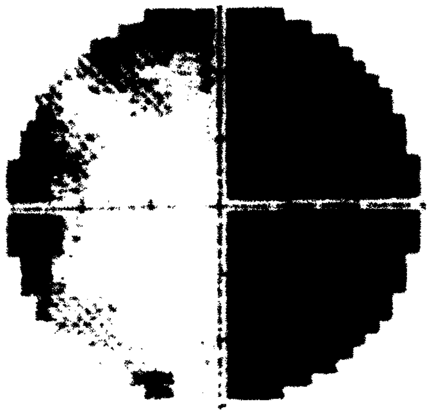
*Fig. 8A* Baseline
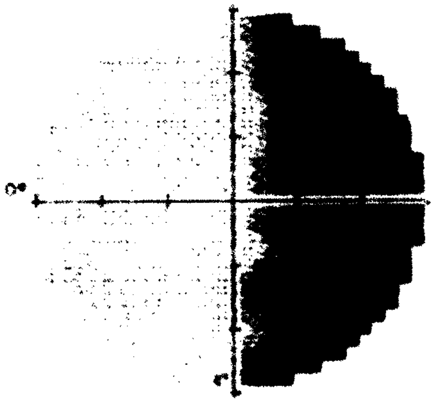
*Fig. 8B* After 2 months (17 sessions)

VISION TRAINING METHOD AND APPARATUS

This application is a continuation of application Ser. No. 12/955,573, filed on Nov. 29, 2010 now abandoned, which claims priority under 35 U.S.C. 119(e) from provisional patent application Ser. No. 61/264,781 filed on Nov. 27, 2009. The entire contents of these applications are incorporated herein by reference for all purposes.

BACKGROUND OF THE INVENTION

1. Field of the Invention

The present invention relates to an apparatus and methodology to retrain visual function in patients who have sustained damage to areas of visual processing in the brain.

2. Background Art

A longstanding belief in neurology is that visual recovery after cortical damage must either occur spontaneously (within a few months of the insult) or not at all. Therefore, therapeutic interventions have typically involved the patient's lifestyle adaptation to his visual impairment (via use of a cane or compensatory prisms to bring portions of the blind field into the view of the remaining sighted portions).

Nevertheless anecdotal reports of "visually guided" performance, such as successfully reaching and grabbing a flickering light in the dark by "blind" patients (Riddoch phenomenon) suggested the existence of unconscious visual processing even in the absence of subjective sight. Electrophysiologically, numerous topographic visual maps have been identified in the brain, only a few of which are related to conscious appreciation. Correspondingly, the presence of a VEP (visually related electrical brain response) has been documented in cases of behavioral blindness (Bodis-Wollner et al. 1977) indicating the continued visual function of these non-conscious areas.

In recent years, this phenomenon of unconscious visual processing, called "blindsight" has been investigated in both humans and animals. Human subjects were generally stroke or accident victims who lost all or a substantial portion of their visual fields. The animals had been surgically altered to eliminate all cortex associated with conscious vision.

Whereas both human and animals showed visual improvement over the course of these studies, recovery in animals was substantially greater and included discrimination of brightness, form and color location, orientation and spatial frequency (monkeys: Miller, 1979: Pasik, 1982; Humphrey & Weiskrantz, 1967). In many cases, animals were restored to visually guided behaviors such as accurately reaching for small stationary targets (Humphrey, 1970).

A major difference between human and animal work (possibly accounting for the huge difference in outcome) is the presence of feedback and active training in animals. In human work (which was more exploratory than remedial), visual stimuli were always extremely brief (generally less than the latency of an eye movement). Subjects who successfully located these stimuli were not given immediate feedback; only at the end of a testing session were they surprised to learn of their greater than chance performance.

Nevertheless, because some improvement in humans has resulted even under these stringent conditions, prior art has been developed to mimic the laboratory paradigm of simply presenting lights for the patient to detect. For example patent document No. DE-U 93 05 147 issued to Schmielau, describes a visual training device which consists of a large dome containing arrays of small light bulbs on its inner surface. These lights are illuminated according to pre-designated sequences (and at different eccentricities from a central fixation point). Although this device does allow assessment and passive training of the visual field, its practicality is limited by (1) very large size, (2) the inflexible locations/sizes of the visual stimuli (3) limitation of presenting only lights (to stimulate "on" cells in the visual system, whereas half the visual system consists of "dark" detectors). The creation of such "dark" targets is difficult to manage in a dome construction. However, it has been shown that animals trained only to find bright targets (on a dark background) did not respond consistently to dark objects on a white background (Humphrey, 1970).

Sable (U.S. Pat. Nos. 6,464,356, 7,367,671 and 7,753,524 introduced and extended the application of computer controlled visual training, arguing the advantages of smaller size, flexibility and patient interactivity. Chief features and goals of Sabel appear to have evolved to (1) mapping the visual field to distinguish visual areas of intact function from those in which vision is degraded or absent (2) the storage of this map for future use, and (3) a computer based algorithm which uses this map to ensure presentation of training targets to preselected areas. In contrast the earlier work (U.S. Pat. No. 6,464,356) is concerned mainly with presenting the target within blind areas or zones of deteriorated vision. In U.S. Pat. No. 7,367,671, visual information such as letters and/or words are simultaneously presented to the sighted field. U.S. Pat. No. 7,753,524 also concerns the portion of the field which is to be stimulated and extends the type of visual target to include colors and spiraling stimuli.

Recent evaluations of the techniques developed by Sabel (and currently marketed under the name of Nova Vision VRT™ (Visual Restoration Therapy™) Nova Vision, Boca Raton, Fla.) have raised the following criticisms:

1. Possibility that target detection involves cues from scattered light impinging upon the good field.
2. Problems of fixation and the probability that small eye movements assisted in target location.
3. No control for false positives (over-responding).
4. Testing is in the same apparatus as training, making it unclear if reported improvement is genuine or generalizes to "real life".
5. Curiosity as to why a small brief white light should be a more effective training stimulus than the rich, complex visual world in which the patient is constantly immersed (Horton, 2005).

As an intended improvement upon the Sabel techniques, Huxlin (U.S. Pat. No. 7,549,743) created a vision training device with the following features:

1. Use of moving stimuli, which are believed to be more effective than stationary lights in stimulating the cortical and sub-cortical cells of the visual system. Huxlin employs random dot kinematograms of which some proportion (from 0-100%) of the small dots move in the same direction.
2. Reduction in stray light cues by using dots of luminance equal to or less than the background.
3. Comparing two anopic areas, one to be trained and the other to serve as a control.
4. A discrimination task which requires the subject to indicate the direction of motion on a keyboard
5. Sequential training of successive adjacent fields. (When motion discrimination in a small area is considered to be substantially improved, an adjacent area is then selected for training).
6. In some embodiments, auditory feedback is provided to indicate a correct keyboard response.

7. In some embodiments, the target is a contrast modulated sinusoidal grating.
8. In some embodiments, the data input device includes an eye tracker.

According to Huxlin et al., when patients attend to visual stimuli in a stationary environment, they show improved motion awareness in the blind hemifield.

Both the Sable and Huxlin techniques share the following features:

1. Selection of delimited training zones within the blind field.
2. Brief target durations (100-500 ms) to avoid errant eye movements.
3. Sessions comprising several hundred trials.
4. Patient's response indicated by a button press.
5. Absence of feedback which might aid in target detection.

When the task objective is either to map or precisely stimulate the field, the steady fixation of the prior art is crucial. Thus, Sabel and Huxlin involve ways of insuring fixation upon a specific portion of (or immediately beside) the computer screen. However, physical intimacy of the fixation point with the screen surface has the inherent drawback of restricting the spatial plane of training to the same depth as the fixation point.

In the prior art, the test stimulus is briefly presented (for approximately 500 milliseconds) and the patient either correctly responds to it or fails to respond. Moments later a new target with different parameters (location or motion) ensues. A training session involves hundreds of trials.

Thus, in the prior art, the patient indicates target detection with a button press. In Sabel, the patient's response speed is fed back to the software as an indirect measure of visual function, e.g., those test areas corresponding to an absent or delayed response are assumed to represent either blind or visually degraded field. Performance feedback is not implemented; Sabel assumes that the mere act of focusing attention upon the blind field is therapeutic.

In Huxlin, one of four keyboard buttons must be pressed to indicate the perceived direction of target motion. This assumes the process of conscious motion discrimination to be the therapeutic element. In some embodiments of Huxlin, an auditory signal serves as feedback to indicate that the correct "motion direction" key was pressed.

SUMMARY OF THE INVENTION

The present advance in the art is based in part on the realization that neither of these prior approaches of Sabel or Huxlin provides information to help the patient identify the target by its temporal characteristic. Nor does either employ the use of feedback to guide the patient in his search for the target.

An important difference between the present approach and prior art is that the present approach uses multimodal stimuli (such as sound and vibration) to accompany each onset of the stimulus, as well as biofeedback principles to train conscious perception.

The present advance in the art is also based on the realization that any device or method which does not provide a "dark-ON" stimulus, does not fully train visual function. Targets employed with the present approach have spatial characteristics to stimulate both light and dark detectors.

Unlike the prior art, the present approach does not involve the mapping of transitional zones or selecting only a portion of the blind field to train. This is because clinical testing has shown the blind field to be non-uniform, with areas of relative sensitivity interspersed with those of deep blindness; a finding that could not be predicted from perimetrically evaluated fields. In addition, the outcome of visual training using the present invention, shows a widening of the entire field (including the sighted hemifield) even when visual targets are randomly presented anywhere within the blind field (and despite the fact that the sighted field is not specifically stimulated), as more fully described below.

Thus, visual training along the transitional borders or within pre-specified portions of the blind field is not therapeutically essential or superior. The present advance in the art therefore, is not concerned with precise field measurement (or storage of such information) to guide target placement.

Since the visual system is replete with detector cells responsive to different depths, the present approach does not confine training to a single plane. Instead, placement of the fixation point is independent of the display screen and can be varied along the x, y, z dimensions, with the only requirement being that it is placed so that the training device falls into the perimetrically blind field. In rare cases of complete cortical blindness, the patient is positioned to face the display monitor without regard to a specific fixation point.

In the present approach, large unauthorized departures from fixation (by more than 2 degrees of visual angle from the fixation point) are interpreted as "cheating" (e.g., seeking the target by using the intact (sighted) field). These eye movements give rise to an audible warning tone and voice feedback for the patient to "look straight ahead". However, an important feature of the present approach is that at specific times during training, errant eye movements are both permitted and encouraged by programmed voice instruction. This occurs only after the patient has successfully located and worked (generally, at least 30 seconds) with the target; the patient is then told to abandon his fixation and to examine the target with his good field. This enables the patient to establish a cognitive relationship between the differing appearance of the target to his blind and sighted fields. After this experience the patient returns to the task of locating the target within the blind field.

In accordance with the present approach, the same (temporally changing) target is repeatedly cycled for a flexible but relatively long duration (generally determined entirely by the patient). A new trial begins only when the patient initiates it with a key press. Thus, an easily detected target might be viewed for a few seconds before the next trial is initiated. A target which is not detected, will be displayed for as long as the patient wishes. It has been determined that new patients need upwards of five (and frequently twenty) minutes with a single target in order to understand/recognize it. Thus, an hour's session may involve working with only a few targets for very long durations.

In accordance with the present approach, presentation of the visual stimulus is always accompanied ("shadowed") by a stimulus of another modality which exactly mimics the temporal characteristics of the target. For example, if the visual target has a frequency of 0.5 Hz, then the companion ("shadow") click or vibration occurs in synchrony with this visual target. The purpose of this non-visual accompaniment is to aid the patient in knowing "what he is seeking". On a neurological level, it is believed that because sound, touch and kinesthetic input are all capable of modifying the responses of primary visual cells, this non-visual input will provide an additional and reliable source of excitation for these weakly responding visual cells.

Of particular significance with respect to the present approach is the administration of immediate and continuous sensory feedback to aid in learning. This is based upon the principle that objective feedback must accompany the acquisition of new skills. For example, in learning to drive a car or shoot an arrow, continuous information regarding the road or target must be available so that the driver/archer can evaluate his performance and make the appropriate behavioral adjustments.

Objective information about internal processes is generally absent, so that control over these functions has been believed impossible. However, biofeedback overcomes these limitations by reliably associating an external signal with the subliminal biological event. For example, by allowing a patient to "hear" the fluctuation of his blood pressure, he learns to isolate the neural activity reliably associated with increases and decreases (a form of classical conditioning) and to actively control it. In the present design, the subject is enabled to "hear/feel" the accuracy of his visuo-motor estimates of target location to help isolate and identify the visual neural responses specific to the target. For example, in the style of a Geiger counter, feedback indicates the accuracy of his motor search for the target by increasing its temporal frequency as his hand nears the target and decreasing as he goes off course. Correct hand/stylus placement is associated with the maximal and very rapid frequency of audible sound/vibration.

The present approach takes advantage of unconscious visual-motor pathways which are important in the "blind-sight" phenomenon (Perrine & Jeanerod, 1978). The reliable correspondence between hand position, sound/vibration and weak visual information enable the patient to recognize and isolate the unconscious vision-related component of his experience from other neural activity, to strengthen it, and ultimately understand it as sight.

BRIEF DESCRIPTION OF THE DRAWINGS

The foregoing aspects and other features of the present invention are explained in the following description, taken in connection with the accompanying drawings, wherein:

FIG. 3 illustrates a sample menu for patient trials, as well as for some research options.

FIG. 6A and FIG. 6B illustrate empirical data for a first subject (S1), collected during two sessions, (one at baseline and another, after approximately one month of training).

FIG. 6B and FIG. 6D illustrate empirical data for a second subject (S2), collected during two sessions, (one at baseline and another, after approximately one month of training).

FIGS. 8A and 8B illustrate changes in visual field for a second patient from baseline to two months into training (as independently assessed by the Humphrey Perimeter).

DETAILED DESCRIPTION OF THE PREFERRED EMBODIMENTS

Figure 1:
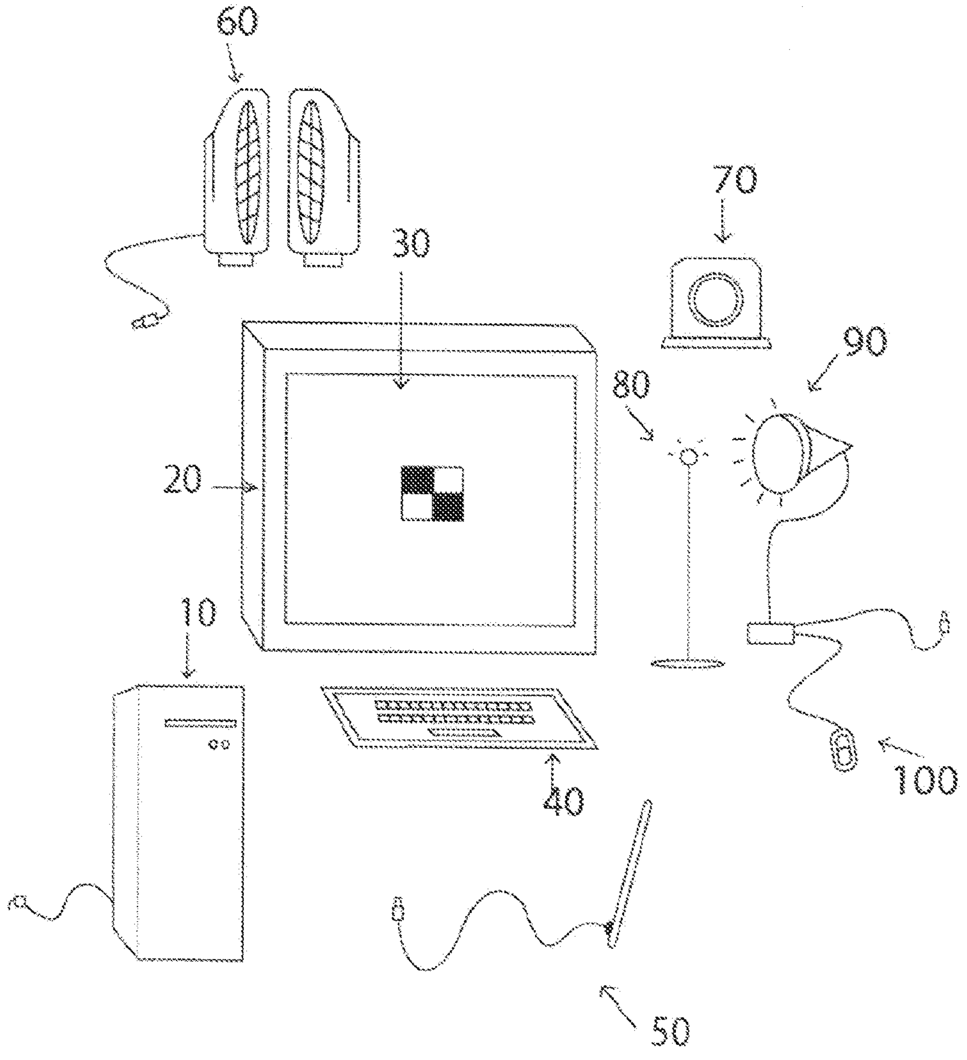
FIG. 1 schematically illustrates an embodiment for a retraining system for patients with post-retinal damage to the visual system.

Although the present invention will be described principally with reference to the single embodiment shown in the drawings, it should be understood that the present invention can be embodied in many alternate forms of embodiments, some of the details of which are also described herein. In addition, any suitable size, shape or type of elements or materials could be used.

The terms "subject" and "patient" both are used herein to refer to an individual using the retraining system and method disclosed herein.

Turning to the drawings and referring to FIG. 1, the preferred embodiment for retraining the visual system is comprised of a conventional computer 10 including a CPU (Central Processing Unit) and having a hard drive containing one or more computer programs in a format executable by the CPU. Other programmable devices which can be used include a game box, or virtual reality device. The computer or other programmable device is connected to the following peripheral devices.

A computer monitor 20 (or any visual display capable of displaying a light or image specified by the programs), for example a CRT, LCD, array of LEDs, OLED, virtual reality goggles and the like is connected to computer 10.

Touch device 30 represents an interface for detecting a patient's hand position (for example, a touch screen overlay (such as is available from Keytec Inc TX, USA)).

Other embodiments may use a light pen (such as is available from Interactive Computer Products, Inc. CA, USA), a photocell, virtual reality glove (also known as a virtual reality glove, a data glove or a cyber glove), or any device known in the art which is capable of responding selectively to the subject's hand position with respect to the a target displayed on monitor 20, as more fully described below.

A keyboard 40 (or any equivalent input device known to the art) is used to initiate and terminate trials.

A stylus 50 is held during the search task assigned to the patient and is capable of communicating hand/target position to the computer 10 and/or providing vibrational feedback to the patient.

In some embodiments, the stylus can be a handheld photocell which responds with increased voltage to increased target proximity. If the monitor 20 *e* is a CRT, the stylus can be a lightpen (such as that made by Interactive Computer Products, Inc).

An embodiment which delivers vibrational feedback requires the conversion of a computer generated algorithm into an electrical pulse pattern. Communication between the computer software and an external vibrator can be accomplished by any interface known in the art for this purpose, for example, the programmable device produced by Phidgets; (SSR Relay Board (Item #3052) and the Phidget Interface Kit (Item #1018)). A commercially available mouse-glove may also be modified for this purpose.

Standard audio speakers 60 are connected to computer 10. Sound intensity can be adjusted to a level which is comfortable to the patient.

An eye movement detector 70, can be any device known in the art, capable of detecting gross eye movements; such detector 70 is commercially available from ISCAN Inc. (Burlington, Mass.). Information regarding eye position is fed back to the software residing on computer 10 to activate instructional voice clips. In the illustrated embodiment, the eye tracking device is mounted above a fixation point, as more fully described below. In some embodiments, the eye tracking device can be worn by the patient.

A fixation point generator, such as a light 80, which can be, for example, a 3 volt red LED activated by a lithium battery is positioned near the borderline of the subject's blind/sighted field. This light (whether freestanding or attached to the computer by sliding/adjustable hinges)—can be positioned anywhere in X, Y, Z space, enabling training to occur at any depth or portion of the visual field. Except when the embodiment involves virtual reality, the fixation point 80 is the only device in FIG. 1 which otherwise does not connect to the computer 10.

A competing stimulus device 90, such as a light, is positioned in the sighted field and has temporal characteristics that are synchronized to the target displayed in the blind field. The competing light 90 can be an LED or visual image capable of rapid recycling at the same rate as the target.

The competing stimulus device 90 displayed in FIG. 1 is an LED encased in a gooseneck lamp frame. Initiation of the voltage output which activates this competing light, is determined by the software, in accordance with pulse supplied by a USB port of computer 10. To meet LED voltage requirements, which can be greater than the 5V USB output, a battery pack may be inserted into the circuit between the USB port and the LED lamp. Software instructions to control the USB output are channeled through the already mentioned Phigets interface system (FIG. 1, numeral 50) although it will be recognized by those familiar with the art, that other means of generating an output pulse (for example through an RS 232 port of computer 10) are possible. In the embodiment of virtual reality, the competing light may be programmed by the software and presented as a virtual image in the sighted field.

A hand held control 100 can regulate characteristics of the light of the competing device 90, and can comprise:

a. An on-off switch; and b. A rheostat to adjust voltage input to the light of the competing device 100 in order to raise or lower its luminance.

Some embodiments may include the following attachments (not shown):

(a) A commercially available chin rest positioning a subject's head a specific distance from the subject monitor and a moveable fixation point.

(b) An adjustable arm rest to enable the patient to comfortably search for targets near the top of the screen.

(c) Color filters and patterned transparencies placed over the competing light

In some embodiments, a hardwired array of bright flashing lights can be used instead of a computer screen.

In some embodiments (particularly in which the subject has limited mobility) this procedure can be adapted to a virtual reality device in which the target and fixation points are projected into virtual space and the patient's limb position is monitored with a virtual reality glove. Virtual reality would allow for the creation of three dimensional targets and fixation points of different depths.

In some embodiments (particularly when the patient has no mobility), the training procedure can be adapted to goggles sensitive to eye position, where correct target localization results in auditory feedback.

Figure 2C:
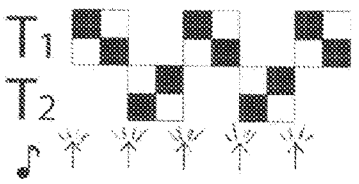
FIG. 2C demonstrates a timeline for target presentation).
Figure 2A:
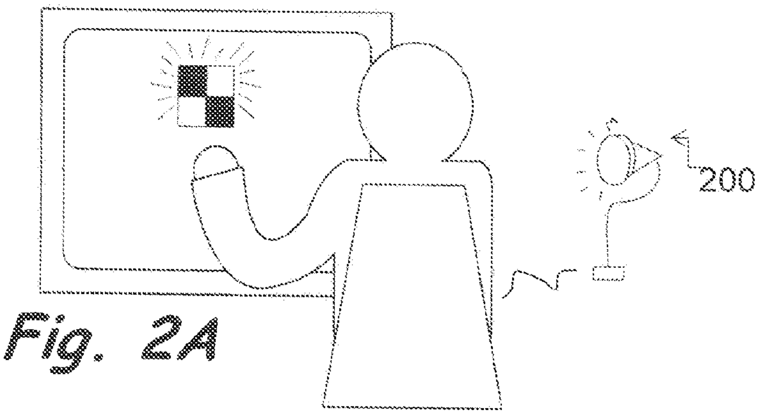
FIG. 2A illustrates the patent seated at the training apparatus.

FIG. 2A shows a patient with left sided blindness seated at the training apparatus. He is facing the fixation point and eye monitor. For a patient with right sided blindness, a mirror image arrangement would be used.

Figure 2B:
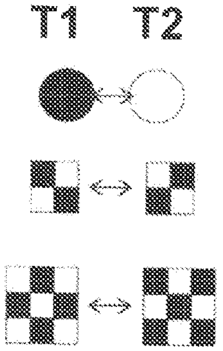
FIG. 2B shows three possible target choices and how each pair appears in its phase reversed-configuration (T1 and T2).

FIG. 2B shows three of the many possible target choices (a circle, or two sizes of checkerboards) and how each pair appears in its two phase reversed configurations (at times T1 and T2).

FIG. 2C illustrates a timeline for target display during which the two phases of target configurations (T1 and T2) alternate in time. In one embodiment, T1 and T2 targets spatially overlap, but they may also be placed in near proximity to give the illusion of movement. In other embodiments, multiple targets may be displayed at the same time, or in close succession so as to mimic motion.

In other embodiments, the T1 and T2 combinations can vary in size and spatial location, so that during the course of a trial, the smallest size travels a short distance (while simultaneously expanding) into the largest size, and then "explodes" (with corresponding sound effects indicating motion and a "pop").

An important component of the present approach is that the target manifests temporal change. This requirement is based upon anatomical data which suggest that the visual neural fibers which detect movement/change are widely distributed in the brain, and that they tend to disproportionately survive insult to the primary visual system (making them important contributors to "blindsight").

Thus, the present concept of "target" is intended to include any type of temporally changing visual stimulus which can be associated with additional non-visual sensory information. The spatial configurations of the target can include all those to which the normal visual system is responsive, including those typically used in vision research, such as sinusoidal gratings, checkerboards, spirals, etc.

As can be seen in FIG. 2C, as represented by the symbol ♪, at the onset of each target presentation, a brief click is played to mimic the temporal frequency of the visual information. For patients with hearing difficulty, a tactile pulse can be synchronized to the visual display frequency.

Figure 2D:
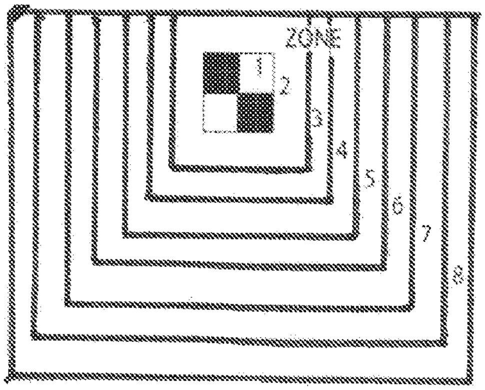
FIG. 2D demonstrates one possible embodiment for determining feedback frequency by associating the target area with concentric distance/reward zones.

FIG. 2D shows one embodiment for search feedback. All targets are associated with concentric distance-related "zones." When the patient's hand touches the zone directly over the target, he is rewarded with a rapidly recycling sound/vibration (which continues as long as his hand is in contact with the screen). Sound feedback is probably sufficient for patients with normal hearing. Vibrational feedback (conveyed via the stylus) is necessary for deaf patients. In some embodiments, both types of feedback can be used simultaneously. It remains to be clinically determined whether the combination of sound and touch feedback is superior to unimodal reinforcement.

In one embodiment, as the patient moves his hand to zones further and further from the DIRECT HIT, the feedback frequency of the sound decreases. Pre-recorded sound clips are associated with each feedback zone.

In other embodiments, the precise distance of the hand to the target can be calculated, for example, by using coordinate data of the guessed position and the actual position of the target, converted by a mathematical algorithm into a pulse frequency, which then activates an external sound generating semiconductor chip and associated circuitry (not shown).

The present approach is intended to include all ways known to those familiar with the art, in which the feedback information can be made to vary according to target position guessed by the patient. With an appropriate command such as a stylus tap, the patient can turn the feedback off or on.

Because reinforcement zones outline the target area, it is possible for the patient to use this multimodal feedback to locate and learn (with his auditory and motor systems) the spatial details (shape/size/spatial envelope of motion) of a visual target, which he cannot see.

In one embodiment, all reward zones (with the exception of the one containing the target) can be deactivated, to aid in the recognition of target boundaries.

FIG. 3A depicts menu options for the target stimuli. The target parameters include the targets (T1 and T2) already described in FIG. 2B, and various options for size, color and temporal frequency. FIG. 3B allows for choice of screen color and contrast with respect to the target. FIG. 3C demonstrates one training protocol for a subject's first experience with the procedure.

In one embodiment, the option for "custom" parameters allows the user to select his own spatial and temporal parameters and also to upload his own visual stimuli. This option is desirable for those conducting research in blindsight and consciousness.

Figure 4:
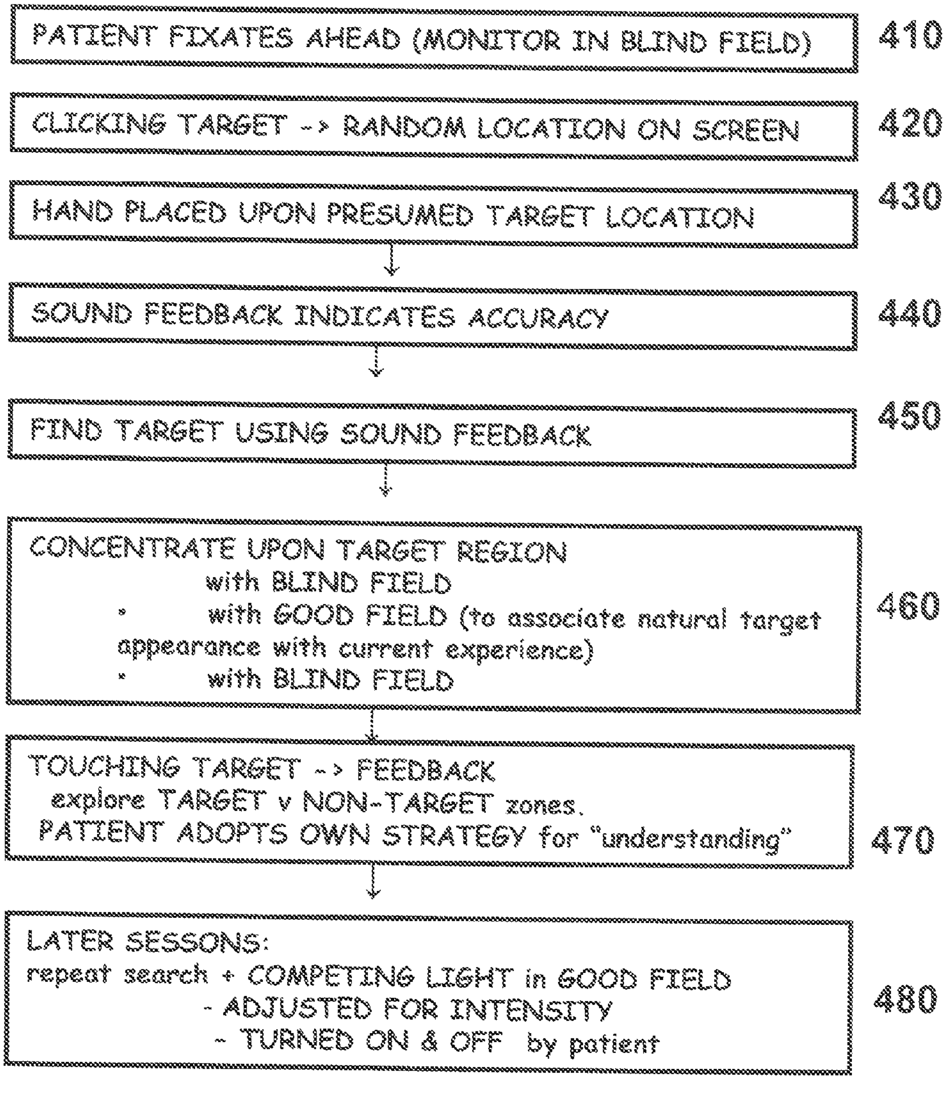
FIG. 4 represents the procedure for a single trial.

FIG. 4 describes a trial format for a subject. While he fixates ahead 410, a clicking target is presented 420 to a random location within his blind field. At 430 he is encouraged to place his hand or the stylus upon the target and to be guided by feedback at 440. Active motor involvement not only maximizes the contribution of unconscious visual-motor pathways to learning, it is more effective than passive activity (i.e. verbal report) in establishing a visual-spatial map (Hein, 1970).

Once the target is located at 450, the subject is encouraged to concentrate upon the target and try to determine why this location is correct. At 460, he may be told to look directly at the target with his sighted field and then return his gaze to fixation. At 470, he is encouraged to manually explore the region around the target and to observe the change in feedback as he deviates from the correct location. The patient may develop his own strategy for "understanding" the location of the target.

In later sessions, as represented at 480 the search can be repeated with a competing light in the sighted hemifield, adjustments may be made in the intensity of the competing light and it may be turned on and off by the patient.

Depending upon the embodiment, the patient can stop/start the reward sound by either lifting and replacing his hand from the screen or by tapping it with the stylus. This allows him to control the reward and to attempt to localize the target without it. In early training, patients report seeing the target only when accompanied by sound. They require substantial experience of placing and withdrawing the hand to enable the image to persist without auditory assistance.

Figure 5:
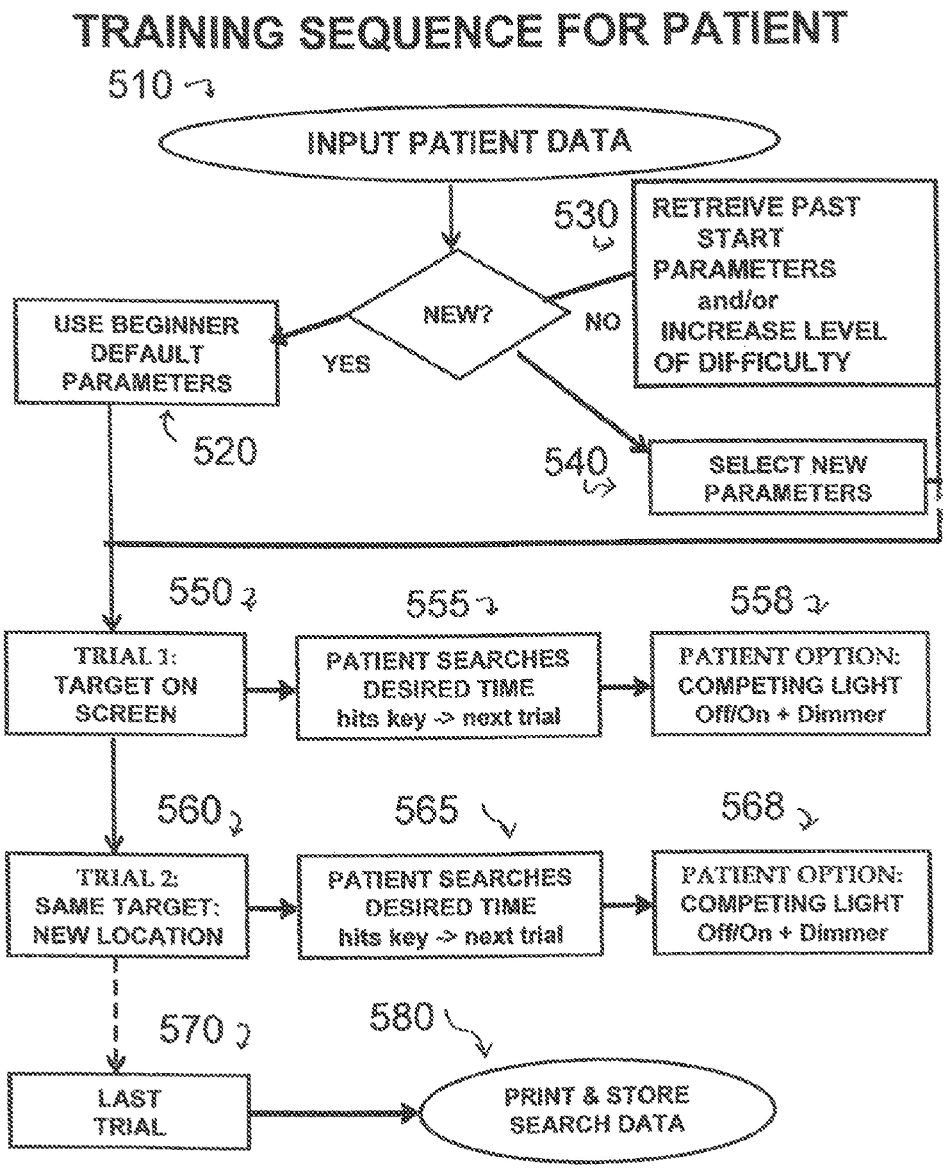
FIG. 5 is a flow chart which demonstrates a sample training sequence.

FIG. 5 shows the format of a training sequence for new and more experienced patients. Patient data is inputted (step 510). New patients typically begin training with the largest, brightest target presented on a black background (step 520). After several sessions, levels of difficulty may be increased (steps 530 and 540).

A first trial is initiated at step 550, during which the patient searches for a desired time, (step 555). At any time during this search, he has the option of using a competing light at step 558, as described below. Or, by hitting the keyboard 40 (FIG. 1), the subject may initiate a new trial (step 560), in which the same target is displayed in a different location. The same sequence of steps is repeated at 565 and 568. This procedure is iterated as many times as the subject desires. A last trial is conducted at step 570. At the conclusion of the session, the search data is printed and stored, at step 580.

Levels of the trials include but are not limited to:

a. Smaller target sizes,
b. Dimmer targets,
c. Counterphasing checkerboard targets of varying spatial frequency,
d. Lower target/background contrast ratios,
e. Increasing the number of simultaneous targets. The patient is required not only to locate them but to bisect the space between them.
f. Presentation of large dark targets (flickering or jiggling) in a small area (on white or grey screens).
g. Competing illumination (of increasing intensity) from the good field.

The use of a competing light in training is based upon the assumption that the blindness experienced by brain-injured patients results from an active suppression generated by the intact brain upon the weak/damaged areas (Richards, 1973). The greater the stimulation of the good brain (e.g., the brighter the room illumination), the more substantial its blinding suppressive effect upon the weaker brain will be (Harrington, 1970). The present technique seeks to regulate this inhibition through the following requirements:

1. Initial training occurs in total darkness where all suppressive input from the good field is absent.
2. Later training involves use of a competing light, which is placed beside the patient, on the side of his good field (as can be seen in FIG. 2A). This competing stimulus may be (but is not limited to) a light that flickers in synchrony with the test target.

Regarding the competing light, the patient can a. control its size, color, and pattern information (by using masks, filters and transparent overlays, respectively) and spatial position (by moving it closer or further).
b. regulate its luminance and/or turn it on and off at will using the control 100 (FIG. 1).

Even after a patient has learned to reliably detect a large target in a dark room, the presence of a dim competing light in the sighted hemifield can totally obliterate the new percept (and cause a sustained inhibition). In a typical trial, the patient will find the target in total darkness, flip on the competing light and (now totally blinded by it), move his hand in the general area of the target, using the other modalities as guides. He will do this for several minutes and when he believes he has restored his percept of the target, he will remove his hand (to eliminate non-visual feedback) and try to recognize it by sight alone.

Typically, the patient who succeeds at locating the target in the presence of the competing light, will subsequently switch it on and off, trying to maintain his percept of the target.

Figures 6A, 6B, 6C, 6D:
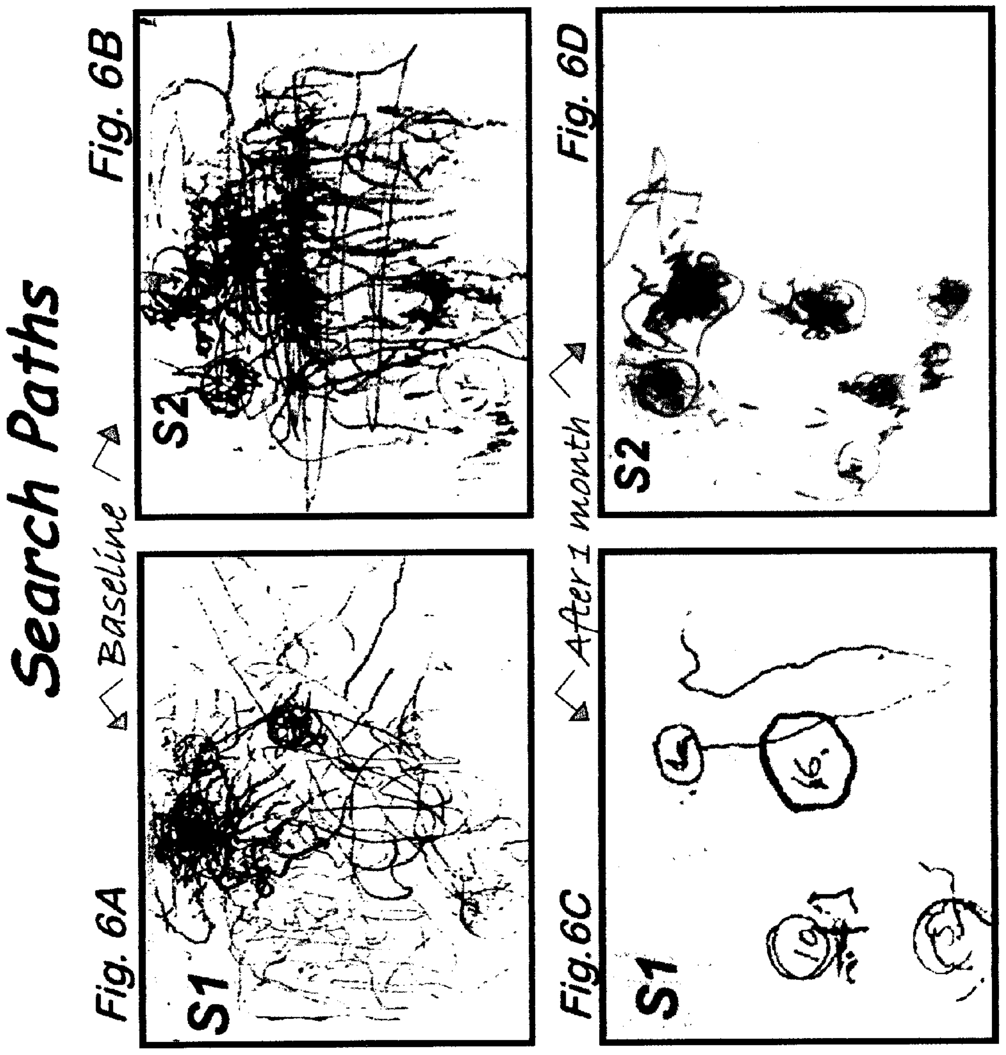

Referring to FIG. 6A and FIG. 6C for a first patient, and to FIGS. 6B and 6D for a second patient, the typical change in search accuracy is shown, from the baseline condition to that noted after one month (approximately 10 hrs) of training.

Each drawing documents all search paths made for several targets in a single sixty to ninety minute session. In the original data, the search path for each target was created in color as the hand moved across the screen (each target having its own associated color path to differentiate it from the search paths for other targets shown in that session).

As can be seen from the baseline data for two different patients shown in the top row, each blind/untrained subject moved his hand widely over the screen, creating a giant (multicolored) scribble. Concentrations of writing can be noted in places of the target location, since these were associated with an auditory reward. The data recorded approximately one month later, were performed under levels of greater difficulty (either with smaller targets (S2) and/or with competition at target onset (S1) than the baseline data). Improvement is defined by the reduction in the randomness of the search, despite an increase in the level of difficulty. Subjective reports of improved target detectability agreed with the greater search precision.

The ability to successfully see the target despite the competing stimulus is accompanied by a widening of the visual field in a lit "real-world" setting. In the case of the patient of FIG. 6C, at about that time, he reported the sudden, brief appearance (in his blind field) of the ignition keys in his father's car.

FIGS. 7A, 7B, 7C and 7D, as well as FIGS. 8A and 8B show the change in visual field for two patients as demonstrated by the Humphrey perimeter. This device presents extremely brief target lights onto a dimly lit background, making it different (and far more difficult than) the training paradigm in which the target is large and presented on a dark background for a long duration.

Both patients suffered occipital infarcts and began training only after two stable visual fields were obtained. This delay in training is methodologically required in order to surpass the critical time period during which spontaneous recovery might be attributable for their improvements. As previously mentioned, without intervention, most functions are believed to stabilize within three to six months after insult. Thus, although early therapeutic intervention is always preferable to delay, (and although some neurological price might be paid by this delay (e.g., cell atrophy or synaptic rewiring)), it is necessary to wait until patients stabilized in order to demonstrate that their improvements can be attributed only to the treatment described herein. Thus, it is likely that the degree of improvement reported here is less than what can be obtained with early intervention.

Figure 7:
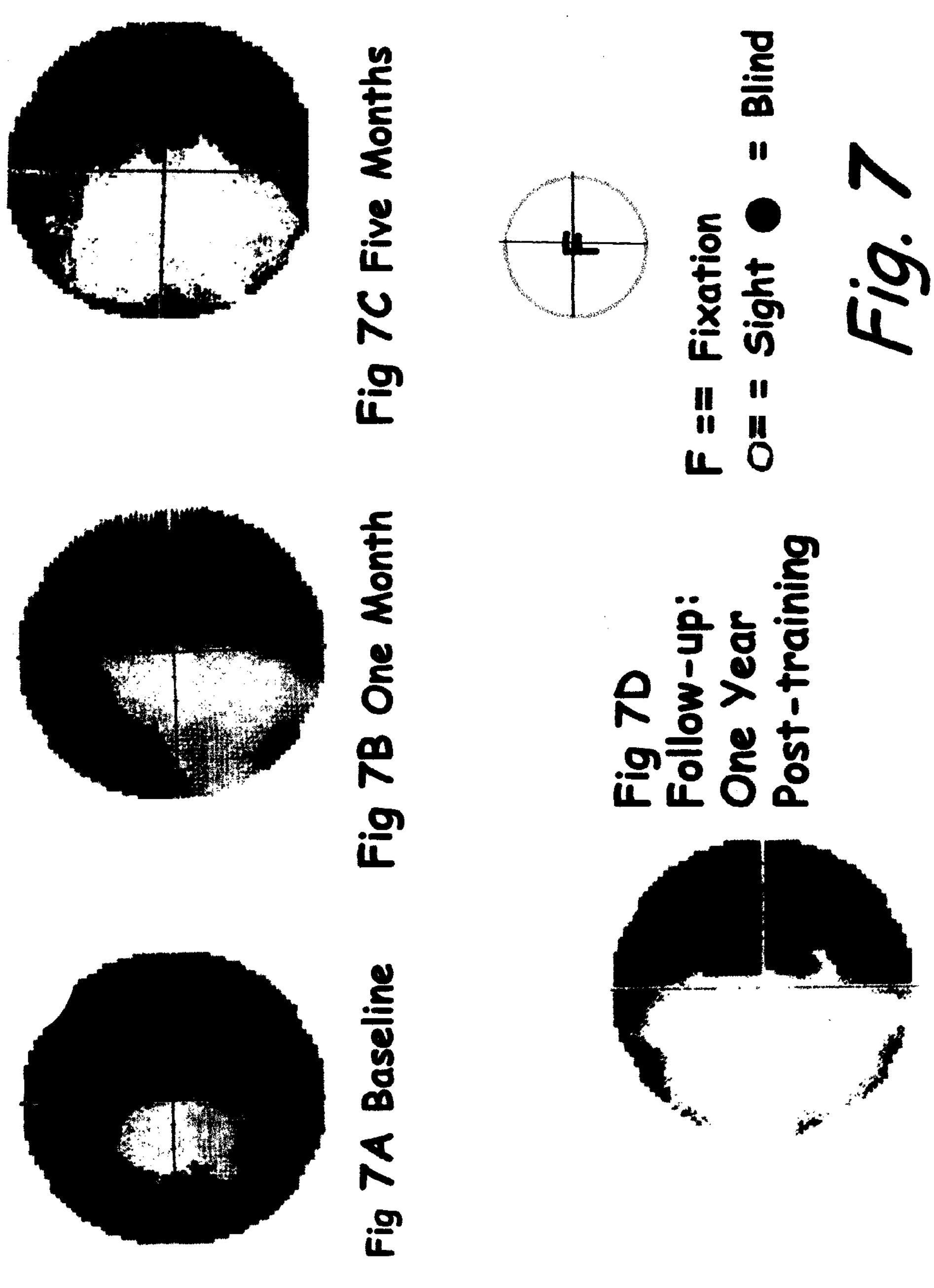
FIGS. 7A, 7B, 7C and 7D illustrate changes in visual field for one patient, from baseline to various points in time points during training, (as independently assessed by the Humphrey Perimeter).

The most extensively studied patient (FIG. 7), was a fifty nine year old surgeon with an occipital infarct due to stroke. CAT scans showed low density areas in the cuneus of the left occipital lobe. Additional effacement was noted in various sites in the left temporal lobe as well as multiple tiny subcortical infarcts below the left frontal and left paracentral lobes. He was first seen ten months post-traumatically (during which time he had been unable to work due to his visual difficulties). His visual field obtained at three months had not changed over the succeeding months, indicating that he had stabilized. He was seen bi-weekly for 1.5-2 hours per session over the course of five months. The four fields presented herein were obtained at baseline (FIG. 7A), after five weeks of training (FIG. 7B), and the last session after five months of training (FIG. 7C). One year after training, a follow-up field was taken (FIG. 7D). Not only was the improvement preserved, but the patient had returned to work doing surgical consulting—which included reading x-rays).

FIG. 8 demonstrates the visual fields of a second patient, a seventy seven year old man with hemi-blindness due to occipital stroke. His CAT scan showed (1) a low density area in the left occipital lobe with effacement of the sulci and (2) obliteration of the left occipital horn. He was first seen fifteen months post-traumatically. His baseline evaluation showed total absence of vision in the right field. After two months of training, (seventeen sessions), his functional field crossed the midline, enabling him to read and to see his entire face in the mirror.

For all patients, the portion of the visual field whose increase can be documented with the Humphrey Perimeter, shows color and form which appears subjectively normal. It should be stressed that in all patients, the expanded vision tends to include the central five degrees, which is the most critical for reading and maximum appreciation of everyday life.

It should also be noted that the search paths shown in FIGS. 6B and 6C, demonstrate a larger functional visual field than is documented by the more stringent conditions of the Humphrey Perimeter. Despite demonstrating what still appears as blindness in part of the visual fields shown in FIGS. 7 and 8, both patients felt safe crossing the street at night, and were well able to detect headlights in the "blind" field.

Data Measurement

In the present approach, the data that is saved, and used in a manner different than that the prior art, includes:

1. session parameters (name, date, target size, etc) so the patient can begin his next session at an appropriate level.

2. a record of hand search movements over the course of a trial. This information is printed after each session and saved in a file which can be displayed later.

The software makes it possible for researchers and clinicians to obtain measures of the time required to locate target (at a given level of difficulty). In general, search time decreases as proficiency improves. However, this information is less meaningful than the search path, since the target can occasionally be located by accident without sight. On other occasions, the patient may delay the immediate search and instead simply contemplate possible target locations without touching the screen until a certain measure of certainty develops.

Trial duration is automatically recorded. In general, less time is spent exploring targets in locations of greater sensitivity. However, a trial could also be rejected if the target is randomly placed in a very similar location as in an earlier trial belonging to the same session. Thus, this information may be less valuable.

Clinical Insights

Results obtained from nine patients, (seven with homonymous hemianopia of longstanding duration (nine months or greater) and two studied at three months after stroke) have contributed to the following understanding:

The blind field is not uniformly blind. If the entire visual field is trainable, some areas will show improvement before others.

After only a few hours of training the patient may report a first "intuition" that "something is there" but he is reluctant to label this experience as visual. This intuition is eventually replaced by a halo which emanates from "somewhere" in the blind field but has no identifiable source. When he locates the target by sound, it may suddenly appear brighter but is still non-localized.

With many more hours of practice, the brightness will seem to be more concentrated and may assume a location in space, either in its true position or it will appear closer to him than it really is.

Sometimes more than one target is experienced; the phantom one being near the border of the sighted field and the true one being on target. On occasion, the two are connected by an imagined arc of light. Over time, the phantom experience lessens.

Early in training, the association of sound and sight are crucial. When the patient withdraws his hand from the screen, the experience of the target lessens. A typical behavior of a patient who has learned to see with the sound feedback, is to concentrate upon the target, occasionally refreshing his image by placing his hand upon it for the sound reinforcement. Later behaviors are to place the hand above the target (without activating sound) and to confirm accuracy by looking with the intact field.

Fluctuation of the visual experience is extremely common. The same target which is mastered at one time during the session, may have to be retrained later that session. This is particularly true after a very difficult condition is introduced; for example, if room illumination is raised. Under this circumstance, an "easy target" may suddenly become invisible for several minutes, even if complete darkness is restored. (This is suggestive of a longstanding inhibitory effect). The general trend is toward improvement over sessions.

Stray light which enters the good field is of little value in pinpointing the target location. The naive subject will report that he sees nothing and that he cannot locate the target except by sound. In cases where stray light is detected, the patient commonly begins his search along the border of his sighted field, surprised by the absence of feedback. For targets far from midline, stray light is frequently unnoticed; a patient may sit beside a brilliant flashing target asking "Tell me when we're ready to start."

Patients who have received about eight to ten hours of training report awareness of moving cars (headlights) at night, and of vague shadows of movement ("ghosts") in the street. After more extensive training, some have reported sudden brief emergence of entire portions of the blind field, such as one's own hand holding the stylus, the dashboard of a car or of an entire white truck suddenly appearing on the blind side. As summarized by one patient "In the same way as I am always breathing without being aware, I was seeing without being aware. This training has made me conscious of that sight."

These reports by patients suggest that this apparatus and method is also useful for research in consciousness.

It should also be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An apparatus for training human vision, comprising:
- a display for viewing by a human subject;
- a programmable device for generating a target on said display, the target being presented for viewing within regions of a visual field of the subject wherein the subject is perimetrically blind or visually impaired;
- a device for the subject to indicate and continuously update, a succession of guessed positions of the target representative of ongoing effort of the subject to locate the target on said display, the succession of guessed positions being used to determine a distance between a currently guessed position and actual target location; and
- a feedback mechanism for providing to the subject updated information representative of distance of the guessed position from the actual location of the target, to enable the subject to find the actual location of the target.

2. The apparatus of claim 1, wherein the programmable device includes one of a computer, a game box, and a virtual reality device.

3. The apparatus of claim 1, wherein the device for the subject to indicate a guessed position of the target includes one selected from the group consisting of a touch screen, a light pen, a photocell and a mouse-glove.

4. The apparatus of claim 1, further comprising apparatus for generating a visual record of the path of successive guessed positions.

5. The apparatus of claim 1, wherein during a trial, the target is repeatedly presented at a location and wherein an auditory click or tactile pulse is produced to occur with presentation of the target and is synchronized to occur simultaneously with target onsets for the entire trial.

6. The apparatus of claim 1, wherein the feedback mechanism provides at least one of audio and tactile information to the subject.

7. The apparatus of claim 6, wherein the audio or tactile information comprises a stimulus having a temporal frequency of occurrence that is inversely related to distance from a guessed position to an actual position of the target.

8. The apparatus of claim 7, wherein the distance of the guessed position from the target is defined by concentric zones positioned around the target.

9. The apparatus of claim 6, wherein the programmable device is programmed with computer code for calculating a separation distance of the guessed position and the target by using coordinate data of the guessed position and the actual position of the target.

10. The apparatus of claim 9, wherein the computer code further comprises a mathematical algorithm for converting the separation distance into a temporal frequency for supplying said stimulus.

11. The apparatus of claim 1, wherein said programmable device is programmed with computer code so that within a trial, the subject can cause the updated feedback information to pause and to resume.

12. The apparatus of claim 1, wherein the programmable device is programmed to display a temporally repeating target, and wherein each presentation of the target is for a time shorter than duration of a trial.

13. The apparatus of claim 12, wherein the programmable device is programmed so that temporal changes of the target occur continuously and repetitively throughout a search trial.

14. The apparatus of claim 12, wherein the programmable device is programmed so that temporal changes of the target include at least one selected from the group consisting of alternations in spatial pattern, spatial composition, shape, color, contrast, luminance, temporal frequency, and spatial position.

15. The apparatus of claim 1, further comprising a fixation target which can be varied in spatial position and upon which the subject fixes gaze while using the apparatus.

16. The apparatus of claim 1, further comprising an eye position monitor for providing data to said programmable device representative of direction of gaze of the subject while using said apparatus.

17. The apparatus of claim 16, wherein the programmable device is programmed with computer code so that eye movements deviating from a fixation direction give rise to an audible voice clip to advise the subject.

18. The apparatus of claim 1, further comprising a source of competing illumination movable to a portion of the visual field wherein the subject is not blind and which is presented simultaneously with the target as the target is presented to a portion of the field wherein the subject is blind.

19. The apparatus of claim 18, wherein the competing illumination is continuously present or temporally modulated in synchrony with the target.

20. The apparatus of claim 18, wherein intensity level and presence or absence of the competing illumination is controlled by the subject.

21. The apparatus of claim 1, wherein the audio or tactile feedback information is continuously available to the subject during the course of a trial.

22. The apparatus of claim 7, wherein the audio or tactile feedback information is continuously available to the subject during the course of a trial.

23. The apparatus of claim 1, wherein duration of a trial is not predetermined.

24. The apparatus of claim 1, wherein the programmable device is programmed so that the subject can initiate and terminate a trial.

25. The apparatus of claim 1, wherein the programmable device is programmed to randomly determine a spatial location of the target in each trial.

26. The apparatus of claim 18, wherein training sessions are organized according to levels of difficulty, in terms of illumination level of the competing stimulus, or target characteristics selected from the group consisting of size, color, luminance, spatial composition, contrast, temporal frequency and number of targets presented in a trial.

27. The apparatus of claim 26, wherein the programmable device is programmed so that the subject selects level of difficulty.

28. The apparatus of claim 18, wherein the device for the subject to indicate a guessed position of the target comprises a virtual input device.

29. The apparatus of claim 18, further comprising means for adjusting illumination level of the competing stimulus.

30. The apparatus of claim 18, further comprising means for adjusting characteristics of the competing stimulus selected from the group consisting of size, luminance, spatial composition, spatial position, color, contrast, and temporal frequency of presentation during a trial.

31. The apparatus of claim 1, wherein the subject can start or stop feedback provided by the feedback mechanism by one of lifting and replacing a hand on the display and by tapping the display with a stylus.

32. The apparatus of claim 1, wherein the display comprises a virtual reality display device and further comprising a virtual reality device for the subject to provide guessed positions of the target.

* * * * *